(12) United States Patent
Zhou et al.

(10) Patent No.: US 6,632,444 B1
(45) Date of Patent: Oct. 14, 2003

(54) STABILIZATION OF FERULIC ACID IN COSMETIC COMPOSITIONS

(75) Inventors: Yan Zhou, Montville, NJ (US); Alexander Lips, Edgewater, NJ (US); Falguni Snehal Nanavaty, Lawrenceville, NJ (US); John Brian Bartolone, Bridgeport, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 101 days.

(21) Appl. No.: 09/625,012

(22) Filed: Jul. 25, 2000

Related U.S. Application Data

(60) Provisional application No. 60/145,674, filed on Jul. 26, 1999.

(51) Int. Cl.$^7$ .............................. A61K 7/00; A61K 4/72; A61K 31/34; A61K 31/19; A01N 57/08
(52) U.S. Cl. ..................... 424/401; 424/59; 514/461; 514/537; 514/567; 514/572
(58) Field of Search ..................... 424/401, 59

(56) References Cited

U.S. PATENT DOCUMENTS

| | | | |
|---|---|---|---|
| 4,792,443 A | * | 12/1988 | Filomeno |
| 5,552,135 A | | 9/1996 | Cioca et al. ............ 424/59 |
| 5,817,299 A | | 10/1998 | Manirazman .......... 424/59 |
| 5,824,326 A | * | 10/1998 | Crotty et al. |
| 6,043,204 A | * | 3/2000 | Kaufman et al. |
| 6,114,377 A | * | 9/2000 | Schnittger et al. |
| 6,180,662 B1 | * | 1/2001 | Lanzendorfer et al. |
| 6,267,971 B1 | * | 7/2001 | Breton et al. |
| 6,432,422 B1 | * | 8/2002 | Yasukawa et al. |

FOREIGN PATENT DOCUMENTS

| | | |
|---|---|---|
| DE | 44 26 952 | 10/1995 |
| DE | 44 21 038 | 12/1995 |
| JP | 6413016 | 1/1989 |
| JP | 05-310526 | * 11/1993 |

OTHER PUBLICATIONS

Derwent Acc. No. 1993–410754, Cell differentiation accelerator–contains ferulic acid (ester), useful for hair tonic and skin care products, (Nov. 1993), abstract of JP 05310526 A.*
The Merck Index, (1976), Merck & Co., INc., (9$^{th}$ ed., Windholz et al.), pp. 581, 1126, & 1127.*
PCT International Search Report in a PCT application PCT/EP 00/06802.
Derwent Abstract of JP 1013016—published Jan. 17, 1989.
Derwent Abstract, JP 5310526, published Nov. 22, 1993.
Derwent Abstract, JP 5255037, published Oct. 5, 1993.

* cited by examiner

*Primary Examiner*—Sreeni Padmanabhan
*Assistant Examiner*—Gina Yu
(74) *Attorney, Agent, or Firm*—Ellen Plotkin

(57) ABSTRACT

Cosmetic compositions containing ferulic acid at a pH of from 3 to 5, in an aqueous phase, along with a polyol, have improved storage stability and dissolution at body temperature.

5 Claims, No Drawings

STABILIZATION OF FERULIC ACID IN COSMETIC COMPOSITIONS

This application claims the benefit of U.S. provisional application No. 60/145,674 filed Jul. 26, 1999.

FIELD OF THE INVENTION

Cosmetic compositions containing ferulic acid in an aqueous phase.

BACKGROUND OF THE INVENTION

Ferulic acid has been described for use in cosmetic compositions as a skin lightener, a sunscreen, skin anti-wrinkling agent, and an anti-oxidant. See for instance JP 6413016, U.S. Pat. No. 5,824,326, U.S. Pat. No. 5,552,135, U.S. Pat. No. 5,817,299, JP 5310526 and JP 5255037. Incorporation of ferulic acid into cosmetic compositions, however, is highly problematic. Ferulic acid is soluble in water at neutral or alkaline pH (i.e., pH 7 and above) but then the solution discolors quickly on storage. At an acidic pH, ferulic acid precipitate into crystals, is deposited in the crystallized form onto skin and therefore cannot be delivered to skin. Thus, incorporation of ferulic acid into an aqueous phase of cosmetic compositions is problematic. On the other hand, ferulic acid is not easily incorporated into an oil phase of emulsions or anhydrous compositions, due to its limited solubility in cosmetically acceptable solvents other than water. Cosmetic compositions which do not discolor on storage and which are able to deliver dissolved ferulic acid to the skin are desirable.

SUMMARY OF THE INVENTION

The present invention includes a cosmetic composition comprising from about 10 to about 100% of an aqueous phase comprising from about 0.01 to about 10% of ferulic acid and from about 1 to about 90% of a non-volatile polyol, with the weight ratio of polyol to ferulic acid being at least 4:1, wherein the pH of the aqueous phase is from about 3 to about 5 and the half-life of the ferulic acid in the composition is at least 20 days at 50° C.

The inventive compositions are aesthetically pleasing, have improved storage ability and attain dissolution of ferulic acid upon application to skin.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

For the avoidance of doubt the word "comprising" is intended to mean including but not necessarily consisting of or composed of. In other words the listed steps or options need not be exhaustive.

The inventive compositions generally contain from 10 to 100% of an aqueous phase. The particular advantage of the inventive compositions is that ferulic acid can be stabilized in an aqueous phase. Thus, the inventive compositions may contain large amounts of water. Preferably, the water is present in an amount of at least 10%, most preferably from 40 to 95% of an aqueous phase. Aqueous phase may optionally contain other water soluble or water miscible solvents or ingredients.

The total aqueous phase is preferably at least 40%, most preferably at least 45%, by weight of the composition.

According to the present invention, the aqueous phase contains from 0.01 to 10%, preferably from 0.1 to 5%, most preferably from 0.5 to 2% of ferulic acid. It is to be understood that depending on the actual pH of the composition, salts of ferulic acid may also be present (e.g., sodium, potassium and ammonium salts).

The composition further contains a non-volatile polyol in an aqueous phase, as a solvent for ferulic acid. The term "polyol" as used in the present invention denotes a non-volatile compound containing more than one hydroxy group. The term "non-volatile" as used herein means that a compound either has a boiling point at 1 atmosphere greater than 130° C., preferably greater than 180° C. or is a solid having a melting point in the range of from 20 to 60° C., preferably 20 to 40° C. Suitable polyols typically have an average molecular weight below 10,000, most preferably below 1,000.

Suitable polyols include but are not limited to propylene glycol, butylene glycol, polyethylene glycol, glycerin, di-propylene glycol, polypropylene glycol, hydroxypropylene glycol, hexylene glycol, 1, 3 butylene glycol, 1,2,6-hexanetriol, ethoxylated glycerin, propyloxylated glycerin, and mixtures thereof. Most preferred non-volatile polyol is selected from polyethylene glycol and propylene glycol, optimally a mixture of the two used to maximize the solubility of ferulic acid and to attain the best sensory properties for the overall composition. When this mixture is employed, the ratio of polyethylene glycol to propylene glycol is in the range of from 5:1 to 1:10, most preferably in the range of from 2:1 to 1:5, with the optimum ratio being 1:2.

By virtue of including a non-volatile polyol solvent in the inventive compositions, dissolution of ferulic acid is achieved either in the composition or, at the very least, after application to skin. Even if the amount of polyol included in the composition is insufficient to dissolve ferulic acid in the composition, after application to the skin, water evaporates and ferulic acid dissolves in the non-volatile solvent left on skin. In the preferred compositions according to the invention, substantially all ferulic acid crystals are dissolved on drying at body temperature.

The amount of polyol in the inventive compositions ranges from 1 to 90%, preferably from 5 to 50%, most preferably from 5 to 30% of the composition, to obtain optimum aesthetic quality and ferulic acid stability and solubility.

The stability of the inventive compositions is achieved by maintaining the pH of the aqueous phase of the compositions in the range of from 3 to 5. Preferably, in order to optimize the stability of ferulic acid in the inventive emulsions, the pH is in the range of from 3 to 4.5, most preferably from 3 to 4. pH may be adjusted by adding acids and bases well known to the one of ordinary skill in the art.

The inventive compositions have a half-life of ferulic acid at least 20 days at 50° C., preferably at least 70 days, most preferably at least 30 days.

"Half-life" is defined as the time it takes for ferulic acid to degrade to half of its original concentration at a given temperature.

The inventive composition may be emulsions (oil-in-water or water-in-oil) or single-phase aqueous compositions (e.g., gels or toners, make-up removers, skin cleansers and aqueous sprays).

Optional Skin Benefit Materials and Cosmetic Adjuncts

The preferred compositions are oil-in-water emulsions, or single-phase aqueous compositions, since the particular advantage of the inventive compositions is the ability to stabilize ferulic acid despite large amounts of water.

If the composition is an oil-in-water emulsion, its oil phase contains oils and/or emollients, and emulsifiers or surfactants.

Suitable oils and/or emollients include but are not limited to silicone oil, vegetable oils, esters, fatty acids and alcohols, and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate, isostearyl palmitate and isopropyl palmitate, and isopropyl myristate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic-and stearyl alcohols and acids.

Exemplary hydrocarbons which may serve as emollients are those having hydrocarbon chains anywhere from 12 to 30 carbon atoms. Specific examples include mineral oil, petroleum jelly, squalene, isoparaffins and squalane.

Oil-in-water emulsions contain from 40 to 99%, preferably from 50 to 95%, most preferably from 70 to 90% of an aqueous phase.

An emollient is included in the inventive oil-in-water emulsions in an amount of from 0.1 to 60%, preferably from 5 to 50%, most preferably from 10 to 30% of the emulsion.

Surfactants or emulsifiers are present to form the inventive oil-in-water emulsion. Total concentration of the surfactant will range from 0.1 to 30%, preferably from 0.1 to 20%, optimally from 0.1 to 10% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include fatty acid soaps, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

It should be understood that oil-in-water emulsions according to the present invention may be co-mixed with other emulsions, including multiple emulsions.

When a preferably inventive composition is a single-phase aqueous composition such as a gel or a toner, skin cleanser, or make-up remover, it further contains a water-soluble thickener, a thickener will usually be present in amounts anywhere from 0.1 to 20% by weight, preferably from about 0.2% to 10% by weight of the composition. Exemplary thickeners are cross-linked polyacrylate gums, such as xanthan, carrageenan, gelatin, karaya, pectin and locust beans gum. Cellulose gums are also used as thickeners such as hydroxy propyl cellulose. Under certain circumstances the thickening function may be accomplished by a material also serving as a silicone or emollient. For instance, silicone gums in excess of 10 centistokes and esters such as glycerol stearate have dual functionality.

The inventive compositions preferably further include an ingredient selected from the group consisting of antioxidants, reducing agents, chelating agents, and mixtures thereof. These ingredients provide an additional level of protection against oxidation of ferulic acid. Common examples of antioxidants, reducing agents and chelating agent for the present formulations can be found in the CTFA International Cosmetic Ingredient Dictionary $4^{th}$ Edition, The Cosmetic, Toiletry, and Fragrance Association, Inc., Washington, D.C., 1991.

Preferable reducing agents are sodium sulfite, sodium bisulfite, sodium metabisulfite, sodium thiosulfite or other thiols, such as thioglycerol, thiourea, thioglycolic acid, cysteine and the like. Preferable antioxidants are propyl gallate, n-propyl trihydroxybenzoate, t-butyl hydroquinone and butylated hydroxytoluene (BHT), butylated hydroxyanisole (BHA), tocopheryl acetate, ascorbyl palmitate, hydroquinone, dibutyl hydroquinone and the like.

Suitable examples of chelating agents include, but are not limited to, EDTA, socium citrate, tartaric acid, organo aminophosphonic acids and organo phosphonic acid components including certain of the commercially available Dequest™ compounds, marketed by Monsanto. Preferred is 1-hydroxyethylene, (1.1-diphosphonic acid).

Organo aminophosphonic acid is an organic compound comprising of at least one phosphonic acid group, and at least one amino group. Suitable organo aminophosphonic acid components for use herein include the amino alkylene poly (alkylene phosphonic acids) and nitrilo trimethylene phosphonic acids. Examples of this type of organo aminophosphonic acid components include certain of the commercially available Dequest™ compounds, marketed by Monsanto.

Preferred are amino tri (methylene phosphonic acid) (Dequest 2006®), diethylene triamine penta (methylene phosphonic acid) and hexamethylene diamine tetra (methylene phosphonic acid).

Other suitable additional heavy metal ion sequestrants for use herein include nitrilotriacetic acid and polyaminocarboxylic acids such as ethylenediaminotetracetic acid, or ethylenetriamine pentacetic acid.

Still other suitable additional heavy metal ion sequestrants for use herein are iminodiacetic acid derivatives such as 2-hydroxyethyl diacetic acid or glyceryl imino diacetic acid.

Antioxidants are included in the inventive compositions in an amount of from 0.01 to 10%, preferably from 0.1 to 5%, most preferably from 0.2 to 4%. Reducing agents are included in the inventive compositions in an amount of from 0.01 to 10%, preferably from 0.1 to 5%, most preferably from 0.2 to 4%. Chelating agents are included in the inventive compositions in an amount of from 0.01 to 1%, preferably from 0.05 to 0.5%, most preferably from 0.05 to 0.3%.

The especially preferred compositions include 0.1% bisulfite, 0.7% Dequest 2006® and 0.2% BHT.

The inventive compositions preferably include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Powders may be incorporated into the cosmetic composition of the invention. These powders include chalk, talc, kaolin, starch, smectite clays, chemically modified lo magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Oil-in-water emulsions are prepared by a typical method to make an emulsion. First, heat up oil phase including emollients, emulsifiers, other oil soluble ingredients such as antioxidants and preservatives, etc., to 70 to 85° C. In a separate container, heat up water phase including water, solvents, water soluble antioxidants, chelators, if added, gums thickeners, etc., to 70 to 85° C. with stirring. Then mix the oil phase, water phase at this temp range while stirring, then cool. Ferulic acid and solvent mixture is pre-heated at 40 to 50° C., until ferulic acid is dissolved, then added into the emulsion at 50° C. with stirring, then cool. Detailed example of the procedure is described in Example 1.

Use of the Composition

The composition according to the invention is intended primarily as a product for topical application to human skin, especially as an agent for skin lightening and conditioning, moisturizing and smoothening the skin, and preventing or reducing the appearance of lined, wrinkled or aged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion, a cream, a gel, cleanser or spray. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following specific examples further illustrate the invention, but the invention is not limited thereto. In all examples, ferulic acid was obtained from ICC (Indofine Chemical Company, Belle Mead, N.J.).

EXAMPLE 1

Cosmetic compositions within the scope of the invention were prepared.

A base formulation shown in Table 1 was made by heating phase A ingredients to 70 to 85° C. with stirring. Phase B ingredients were heated in a separate container to 70 to 85° C. with stirring. Then, phase A was added into phase B while both phases were kept at 70 to 85° C. The mixture was stirred for at least 15 minutes at 70 to 85° C., then cooled.

A base formulation is shown in Table 1.

TABLE 1

| Ingredients | % wt. | Phase |
|---|---|---|
| Isostearyl Palmitate | 6.00 | A |
| C12–C15 Alkyl Octanoate | 3.00 | A |
| PEG-100 Stearate | 2.00 | A |
| Glyceryl Hydroxystearate | 1.50 | A |
| Stearyl Alcohol | 1.50 | A |
| Stearic acid | 3.00 | A |
| TEA, 99% | 1.20 | B |
| Dimethicone | 1.00 | A |
| Sorbitan Monostearate | 1.00 | A |
| Magnesium Aluminum Silicate | 0.60 | B |
| Vitamin E acetate | 0.10 | A |
| Cholesterol | 0.50 | A |
| Simethicone | 0.01 | B |
| Xanthan gum | 0.20 | B |
| Hydroxyethylcellulose | 0.50 | B |
| Propylparaben | 0.10 | B |
| Disodium EDTA | 0.05 | B |
| Butylated hydroxytolene | 0.05 | B |
| Methylparaben | 0.15 | B |
| Water | 51.00 | B |
| Total | 73.46 | B |

Ferulic acid was dissolved in the solvents specified in formulae A–N as shown in. Table 2 at 40 to 50° C. with stirring until ferulic acid is dissolved. Then, ferulic acid/solvent mixture was added into the base formula at 50° C. with mixing. The emulsion is then cooled to 40° C. and added with 2-bisabolol, 0.2% of the total formula.

Finally, the pH was adjusted to 3.8 with hydrochloric acid.

TABLE 2

| | Example Formula No. (weight %), pH = 3.8 | | | | | | | | | | | | | | |
|---|---|---|---|---|---|---|---|---|---|---|---|---|---|---|---|
| Component | A | B | C | D | E | F | G | H | I | J | K | L | M | N | R |
| Base | 73 | 73 | 73 | 65 | 73 | 73 | 65 | 65 | 65 | 65 | 73 | 73 | 65 | 73 | 73 |
| Ferulic acid | 0.5 | 1.0 | 1.0 | 1.0 | 2.0 | 2.0 | 2.5 | 3.5 | 4.0 | 2.0 | 2.0 | 2.0 | 2.0 | 2.0 | 1.5 |
| Propylene glycol | 10 | 0 | 10 | 20 | 0 | 10 | 20 | 20 | 20 | 20 | 10 | 10 | 20 | 10 | — |
| Polyethlene-Glycol 200 | 5 | 0 | 5 | 5 | 0 | 5 | 5 | 5 | 5 | 5 | 5 | 5 | 5 | 5 | — |
| Butylene glycol | 3 | 3 | 3 | 3 | 3 | 3 | 3 | 3 | 3 | 3 | 3 | 3 | 3 | 3 | 3 |
| Glycerin | 2 | 2 | 2 | 2 | 2 | 2 | 2 | 2 | 2 | 2 | 2 | 2 | 2 | 2 | 2 |
| Dimethyl isosorbite | — | — | — | — | — | — | — | — | — | — | 5 | — | — | — | — |

TABLE 2-continued

| | Example Formula No. (weight %), pH = 3.8 | | | | | | | | | | | | | | |
|---|---|---|---|---|---|---|---|---|---|---|---|---|---|---|---|
| Component | A | B | C | D | E | F | G | H | I | J | K | L | M | N | R |
| Na bisulfite | — | — | — | — | — | — | — | — | — | — | — | 0.1 | 0.1 | 0.1 | — |
| BHT | — | — | — | — | — | — | — | — | — | — | — | 0.2 | 0.2 | 0.2 | — |
| Dequest2006 ®* | — | — | — | — | — | — | — | — | — | — | — | — | — | 0.66 | — |
| Water | | | | | | | | balance | | | | | | | |

*Dequest 2006 ® = Amino tri(methylene phosphonic acid)

EXAMPLE 2

The dissolution temperatures of ferulic acid in the cosmetic compositions of the present invention were investigated.

A test composition was applied to a glass slide to form a 35 to 70 mm thick layer. Water was then allowed to evaporate by drying the test composition on a glass slide at room temperature for 45 min. The slide was then inserted into the hot stage of an optical microscope Zeiss Axiopan and observing the temperature at which ferulic acid crystals dissolved in the composition on the slide. The heating rate was 1° C./min in the beginning and then at 0.2° C./min. after a substantial amount of ferulic acid crystals have melted. The melting temperature of ferulic acid crystals in the absence of the solvent is 174° C. The results that were obtained are shown in Table 3.

TABLE 3

| Formula From Table 2 | Ferulic Acid weight % | Polyol weight % | Dissolution temperature of ferulic acid crystals | | Polyols/ Ferulic Acid Ratio |
|---|---|---|---|---|---|
| | | | Before dry | After dry | |
| A | 0.5 | 20 | <RT | <RT | 40:1 |
| B | 1.0 | 5 | 39.6 | 34.6 | 5:1 |
| C | 1.0 | 20 | 34 | <RT | 20:1 |
| D | 1.0 | 30 | 32.9 | <RT | 30:1 |
| E (comparative) | 2.0 | 5 | 58.6 | 79.9 | 25:1 |
| F | 2.0 | 20 | 48 | 26 | 10:1 |
| G | 2.0 | 30 | 44 | 24.9 | 15:1 |
| H | 2.5 | 30 | 47.5 | 28 | 12:1 |
| I | 3.0 | 30 | 55 | 33 | 10:1 |
| J | 4.0 | 30 | 58 | 36 | 75:1 |
| R (comparative) | 1.5 | 5 | 51.3 | 48.2 | 3.3:1 |

The results in Table 3 demonstrate that in the presence of polyol, the dissolution temperature of ferulic acid was reduced, compared to 174° C. (melting temperature in the absence of polyols). Moreover, with the exception of Compositions E and R, when the samples were dried after water had evaporated, ferulic acid crystals melted completely at a much lower temperature than that before drying as a result of local polyol concentration increase, demonstrating the preferred raio range of polyols to ferulic acid in this inventive composition.

EXAMPLE 3

The storage stability of ferulic acid in various cosmetic compositions was measured. Composition were prepared as described in Example 1 except that the pH of composition F was varied for comparison (adjusted by KOH) from pH 3.8 to pH 5.5 as formula F' and pH 7.0 as formula F" as indicated in Table 4. All compositions were stored at 50° C. For comparison, the Working Example 1 that is reported in J01013016 was duplicated and stored at the same temperature. Discoloration of all samples was examined visually and chemical stability of ferulic acid in all samples was analyzed by a HPLC method. The HPLC analysis of ferulic acid used Column Regis ODS II, reversible (150×4.6 mm). Mobile phase was 35/65 Methanol/water plus 1 ml /L acetic acid. Flow rate was 1.0 ml/min. UV detector was used to detect ferulic acid at 265 nm. Injection volume was 10 μL. Standard sample was dissolved in 35/65 methanol/water with a concentration range from 2 to 10 ppm. Elution time was 8 minutes.

TABLE 4

| Formula | pH 50° C. | Discoloration 1 month, 50° C. | Chemical Stability %, remaining ferulic acid | |
|---|---|---|---|---|
| | | | 1 week, 50° C. | 1 month 50° C. |
| Comparison - working example 1 in J01013016 | 7.0 | Yes, overnight turns yellow | 70 | 1.9 |
| A | 3.8 | No | 100 | 100 |
| C | 3.8 | No | 100 | 100 |
| D | 3.8 | No | 100 | 100 |
| F | 3.8 | No | 100 | 91 |
| F'-comparison | 5.5 | Yes, yellow | 72 | |
| F"-comparison | 7.0 | Yes, brown | 64 | 36 |
| K | 3.8 | Yes, yellow | | 65 |
| L | 3.8 | No | | 97 |
| M | 3.8 | No | | 95 |
| N | 3.8 | No | | 98 |

The results in Table 4 demonstrate that the lower the pH of the composition, the better ferulic acid stability. Composition claimed in J01013016, which falls outside the scope of this invention, was not chemically stable and discolored overnight at 50° C. In addition, the composition containing dimethyl isosorbide gave poor ferulic acid stability (formula K), demonstrating that despite the low pH, some ingredients (e.g., dimethyl isosorbide) may destabilize ferulic acid. The results in Table 4 also demonstrate that the addition of antioxidants and chelating agents to the compositions of this invention provided additional stability (L,M and N).

EXAMPLE 4

In this example, stability of additional ferulic acid-containing compositions was examined. Also, ferulic acid solubility was investigated. The formulations are listed in

TABLE 5

| Component | weight % O | Q-Comparison |
|---|---|---|
| Ferulic acid | 2.0 | 2.0 |
| Propylene glycol | 45.0 | |
| Butylene glycol | 5.0 | |
| Polyethylene glycol 200 | 5.0 | 98.0 |
| Hydoxy propyl cellulose | 0.5 | |
| Water | 43.2 | |
| BHT | 0.2 | |
| Na$_2$SO$_3$ | 0.1 | |
| Ethanol | | |
| pH of the composition | 4.7 | |

The same storage conditions as described in Example 2 were used and the stability results are shown in Table 6.

TABLE 6

| Formula | Discoloration 1 week 50° C. | 1 month 50° C. | Crystallization of ferulic acid |
|---|---|---|---|
| O | No | No | No |
| Q-Comparison | Yellow | Very Yellow | No |

The results in Table 6 demonstrate that formulae O and P had good storage stability while formula Q did not.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic composition comprising:

from 10 to 100% of an aqueous phase consisting essentially of from 0.01 to 10% of ferulic acid and from 1 to 90% of a non-volatile polyol, with the weight ratio of polyol to ferulic acid being at least 4:1;

wherein the pH of the composition is from about 3 to about 5 and the half-lifetime of the composition is at least 20 days at 50° C.;

and wherein said ferulic acid is in crystalline form at room temperature.

2. The composition of claim 1, wherein the composition is an oil-in-water emulsion.

3. The composition of claim 1, wherein the polyol has an average molecular weight below 10,000 Daltons.

4. The composition of claim 1, wherein the composition further comprises anti-oxidants, reducing agents and chelating agents.

5. A cosmetic composition comprising:

from 10 to 100% of an aqueous phase consisting essentially of from 0.5 to 10% of ferulic acid and from 1 to 90% of a non-volatile polyol, with the weight ratio of polyol to ferulic acid being at least 4:1;

wherein the pH of the composition is from about 3 to about 5 and the half-lifetime of the composition is at least about 1 month at 50° C.

* * * * *